United States Patent
Creaven et al.

(10) Patent No.: US 7,850,910 B2
(45) Date of Patent: Dec. 14, 2010

(54) COMPACT FOLDABLE METER

(75) Inventors: John P. Creaven, Granger, IN (US); William W. McCloud, Elkhart, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 32 days.

(21) Appl. No.: 12/084,855

(22) PCT Filed: Nov. 10, 2006

(86) PCT No.: PCT/US2006/044013
§ 371 (c)(1), (2), (4) Date: May 12, 2008

(87) PCT Pub. No.: WO2007/059048
PCT Pub. Date: May 24, 2007

(65) Prior Publication Data
US 2009/0162248 A1    Jun. 25, 2009

Related U.S. Application Data

(60) Provisional application No. 60/736,429, filed on Nov. 14, 2005.

(51) Int. Cl.
*G01N 21/00* (2006.01)
(52) U.S. Cl. .................. 422/58; 600/584; 600/583; 705/2; 705/1; 705/3; 422/50; 422/56; 422/63; 422/102; 422/82.01
(58) Field of Classification Search ......... 606/181–183, 606/583; 422/68.1, 58
See application file for complete search history.

(56) References Cited

U.S. PATENT DOCUMENTS

| 5,856,195 | A  | * | 1/1999  | Charlton et al. | ........... 436/50 |
| 7,092,891 | B2 | * | 8/2006  | Maus et al.     | ............ 705/2 |
| 7,130,511 | B2 | * | 10/2006 | Riester et al.  | .......... 385/101 |
| 7,150,755 | B2 | * | 12/2006 | Levaughn et al. | .......... 606/181 |
| 7,582,063 | B2 | * | 9/2009  | Wurster et al.  | .......... 600/584 |
| 2004/0048394 | A1 |   | 3/2004  | Kirchhevel   | .......... 436/183 |
| 2005/0065539 | A1 |   | 3/2005  | Muser        | .......... 606/161 |

FOREIGN PATENT DOCUMENTS

EP    1 279 365 A2    1/2003

OTHER PUBLICATIONS

Written Opinion corresponding to International Patent Application Serial No. PCT/US2006/044013, European Patent Office, dated Apr. 2, 2007; 6 pages.

International Search Report corresponding to International Patent Application Serial No. PCT/US2006/044013, European Patent Office, dated Apr. 2, 2007; 4 pages.

* cited by examiner

*Primary Examiner*—Jill Warden
*Assistant Examiner*—Sally A Sakelaris
(74) *Attorney, Agent, or Firm*—Nixon Peabody LLP (57) ABSTRACT

A foldable instrument (10) adapted to determine an analyte concentration of a fluid sample using a test sensor is disclosed. The instrument comprises a first portion (12) including a display (22) and a second portion (14) pivotally coupled to the first portion by a pivot mechanism (23). The second portion includes a user-interface mechanism (16a-c). One of the first portion (12) and second portion (14) includes at least one opening (18) formed therein. The opening is adapted to receive a test sensor. The instrument is adapted to be folded into a closed position and unfolded into an open position by rotating one of the first portion and second portion about the pivot mechanism (23).

22 Claims, 7 Drawing Sheets

Fig. 8 ated, or unfolded, position and a closed, or folded, position. In the open position, the meter is adapted to receive a test sensor.

COMPACT FOLDABLE METER

CROSS-REFERENCE TO RELATED APPLICATIONS

This application is a U.S. national phase of International Application No. PCT/US2006/044013, filed Nov. 10, 2006, which claims the benefit of priority of U.S. Provisional Application No. 60/736,429 filed on Nov. 14, 2005, which is incorporated by reference in its entirety.

FIELD OF THE INVENTION

The present invention generally relates to a compact device that is adapted to determine at least one analyte concentration in a fluid sample. More particularly, the invention relates to a compact, foldable meter adapted to be used to determine at least one analyte concentration in a fluid, for example, blood glucose.

BACKGROUND OF THE INVENTION

The quantitative determination of analytes in body fluids is of great importance in the diagnoses and maintenance of certain physiological abnormalities. For example, lactate, cholesterol, and bilirubin should be monitored in certain individuals. In particular, determining glucose in body fluids is important to diabetic individuals who must frequently check the glucose level in their body fluids to regulate the glucose intake in their diets. The results of such tests can be used to determine what, if any, insulin or other medication needs to be administered. In one type of testing system, test sensors are used to test a fluid such as a sample of blood.

Many individuals test their blood glucose several times per day. Thus, the individuals often must carry with them a meter for determining the glucose concentration of their blood. The individuals may also carry with them other analyte-testing instruments, including test sensors, a lancet, disposable lancets, a syringe, insulin, oral medication, tissues, or the like. Thus, the individuals are able to perform testing of their blood glucose at different locations including their homes, places of employment (e.g., office buildings or work sites), places of recreation, or the like. Carrying the meter and/or other analyte-testing instruments to these various locations may be inconvenient for the individual. The inconvenience is amplified by the fact that, oftentimes, the meter may be large, bulky, and/or heavy.

It would be desirable to have a compact device for determining an analyte concentration that assists in addressing one or more of the above disadvantages.

SUMMARY OF THE INVENTION

According to one embodiment of the present invention a foldable instrument adapted to determine an analyte concentration of a fluid sample using a test sensor is disclosed. The instrument comprises a first portion including a display and a second portion pivotally coupled to the first portion by a pivot mechanism. The second portion includes a user-interface mechanism. One of the first portion and second portion includes at least one opening formed therein. The opening is adapted to receive a test sensor. The instrument is adapted to be folded into a closed position and unfolded into an open position by rotating one of the first portion and second portion about the pivot mechanism.

According to another embodiment of the present invention, a foldable instrument adapted to determine an analyte concentration of a fluid sample using a test sensor is disclosed. The instrument comprises a main housing including a first portion and a generally parallel second portion. The second portion is coupled to the first portion by a wall portion. The instrument further comprises a middle portion positioned between the first portion and the second portion. The middle portion includes at least one opening formed therein. The opening is adapted to receive a test sensor. The middle portion is pivotally coupled to at least one of the first portion and the second portion by a pivot mechanism. The instrument further comprises a display positioned on one of the first portion and the middle portion. The instrument further comprises a user-interface mechanism positioned on one of the first portion and the middle portion not including the display. The instrument is adapted to be folded into a closed position and unfolded into an open position by rotating at least one of the main housing and the middle portion about the pivot mechanism.

The above summary of the present invention is not intended to represent each embodiment or every aspect of the present invention. Additional features and benefits of the present invention are apparent from the detailed description and figures set forth below.

BRIEF DESCRIPTION OF THE DRAWINGS

FIG. 2b is an exploded view of the meter of FIG. 2a.

FIG. 5b is a top view of the cartridge of FIG. 5a.

DETAILED DESCRIPTION OF THE ILLUSTRATED EMBODIMENTS

Figure 1A:
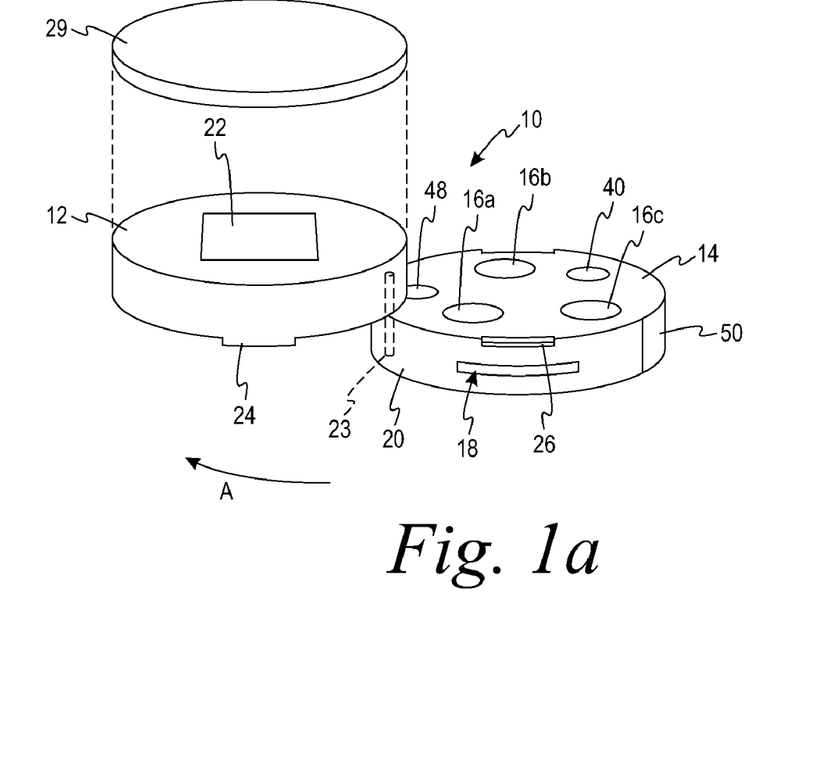
FIG. 1a is a top perspective view of a meter in an open position according to one embodiment of the present invention.

The present invention is directed toward a compact, foldable meter that determines an analyte concentration in a fluid. FIGS. 1a,b, 2a,b, 3a,b, and 4a,b depict respective compact, foldable meters according to embodiments of the present invention. The meter is used to determine concentrations of analytes. Analytes that may be measured using the present invention include glucose, lipid profiles (e.g., cholesterol, triglycerides, LDL, and HDL), microalbumin, hemoglobin $A_1C$, fructose, lactate, or bilirubin. The present invention is not limited, however, to these specific analytes, and it is contemplated that other analyte concentrations may be determined. The analytes may be in, for example, a whole blood sample, a blood serum sample, a blood plasma sample, or other body fluids like ISF (interstitial fluid) and urine. One non-limiting example of the meter's use is to determine the glucose concentration in a user's blood or plasma.

Figure 1B:
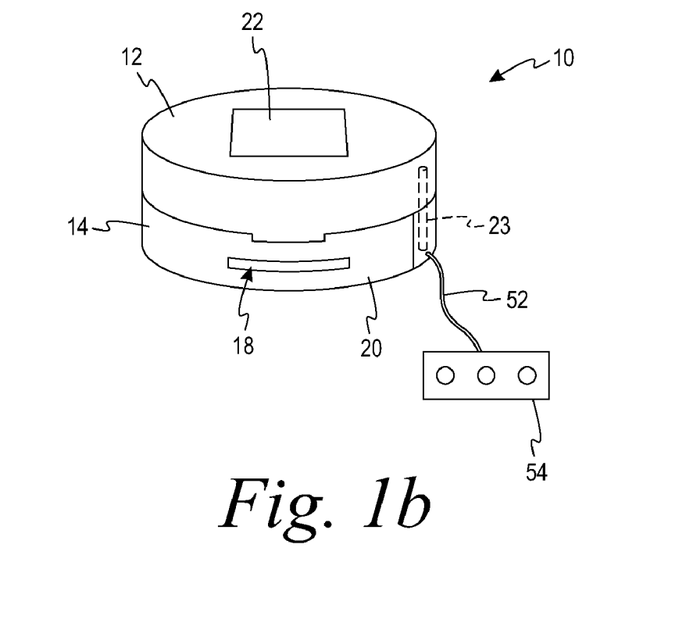
FIG. 1b is a top perspective view of the meter of FIG. 1a in a closed position.

Referring to FIGS. 1a,b, a meter 10 according to one embodiment of the present invention is shown. Although the cross sections of the meters of the illustrated embodiments are generally circular, it should be noted that the cross section of the meters used herein may be other shapes such as square, hexagonal, octagonal, other polygonal shapes, or oval. The meter 10 is typically made of a polymeric material. Non-limiting examples of polymeric materials that may be used in forming the meter 10 include polycarbonate, ABS, nylon, polypropylene, or combinations thereof. It is contemplated that the meter 10 may be made using non-polymeric materials.

The meter 10 includes a first portion 12 and a second portion 14. The first portion 12 and the second portion 14 have generally the same diameter. The meter 10 is desirably sized so that it may fit generally within a user's purse or pocket. Thus, it is desirable that the meter 10 have a diameter of less than 2 inches to enhance portability. It is also desirable that the meter 10 have a footprint area of less than about 5 $in^2$. The meter 10 may even have a footprint area of about 3 $in^2$.

The second portion 14 includes a user-interface mechanism. In the illustrated embodiments, the user-interface mechanism includes at least one button 16a-c. At least one of the user-interface buttons 16a-c may be depressed to operate electronics of the meter 10. The meter 10 typically includes a microprocessor or the like for processing and/or storing data generated during the testing procedure. For example, the user-interface buttons 16a-c may be depressed to activate the meter 10, to recall and view results of prior testing procedures, to input meal and/or exercise indicators, or the like. It is contemplated that other user-interface mechanisms may be used, including, but not limited to, scroll wheels or the like.

At least one of the first portion 12 and second portion 14 forms at least one opening 18 therein. In FIGS. 1a,b, the opening 18 is located on a side surface 20 of the second portion 14. The opening 18 is adapted to receive and/or hold a test sensor and assist in determining the analyte concentration of a fluid sample.

To communicate at least the analyte concentration to the user, the meter 10 includes a display 22 positioned on the first portion 12. One example of a display 22 that may be used in the meter 10 is a liquid-crystal display. The liquid-crystal display typically shows information from the testing procedure and/or in response to signals input by the user-interface buttons 16a-c.

Because the display 22 is positioned on the first portion 12, while the user-interface buttons 16a-c are positioned on the second portion 14, the display 22 may generally span a majority of the surface of the meter 10, which is especially desirable since the meter 10 itself is relatively small and compact. Thus, the display 22 may be relatively large, assisting in the readability of the information displayed on the display 22. The display 22 may, for example, have an area of at least about 1 $in^2$, such as 1 inch×1 inch. The display 22 may even have an area of at least about 1.613 $in^2$, such as 1.27 inch×1.27 inch. Some of the information that may be shown on the display 22 includes, but is not limited to, the following: a numerical display, an indication of the number of sensors remaining, an indication to load a cartridge or test sensor into the instrument, an apply-blood indication, a temperature indication, results of prior testing procedures, meal and/or exercise indicators, and/or various combinations thereof. In addition to or instead of the user-interface buttons 16a-c, the meter 10 may also include a navigation button, a scroll wheel, or another mechanism suitable for scrolling through the information displayed on the display 22.

The meter 10 may be powered by a mains power supply, a battery, or any other suitable power source. The mains power supply may include internally operated AC and/or DC power supplies. It may be desirable that the meter 10 be powered by battery due to the portable nature of the meter 10. The battery may be housed within one of the first portion 12 and the second portion 14. In another embodiment, the meter 10 is rechargeable via mains power.

According to the present invention, the meter 10 has a "foldable" feature, in which the second portion 14 is pivotally coupled to the first portion 12 via a pivot mechanism 23. The pivot mechanism may include a pin around which the first portion 12 and the second portion 14 rotate. It is contemplated that other pivot mechanisms may also be employed. The pivot mechanism allows for the meter 10 to "fold" into a closed position (see FIG. 1b) and "unfold" into an open position (see FIG. 1a). To convert the meter 10 from the open position to the closed position, the second portion 14 may be rotated in a first direction about the pivot mechanism, as shown, for example, by Arrow A in FIG. 1a, until the first portion 12 and the second portion 14 are substantially flush and stacked in the closed position of FIG. 1b. The first portion 12 may also be rotated about the pivot mechanism to convert the meter 10 into the closed position.

The meter 10 of this embodiment may optionally include a feature for maintaining the meter 10 in the open and/or closed position. For example, the meter 10 may be releasably locked in an open or closed position by fitting an at least one raised feature 24 positioned on the first portion 12 within a corresponding at least one recessed feature 26 positioned on the second portion 14. It should be noted that any mechanism suitable for maintaining the meter 10 in an open and/or closed position may be used.

Figure 8:
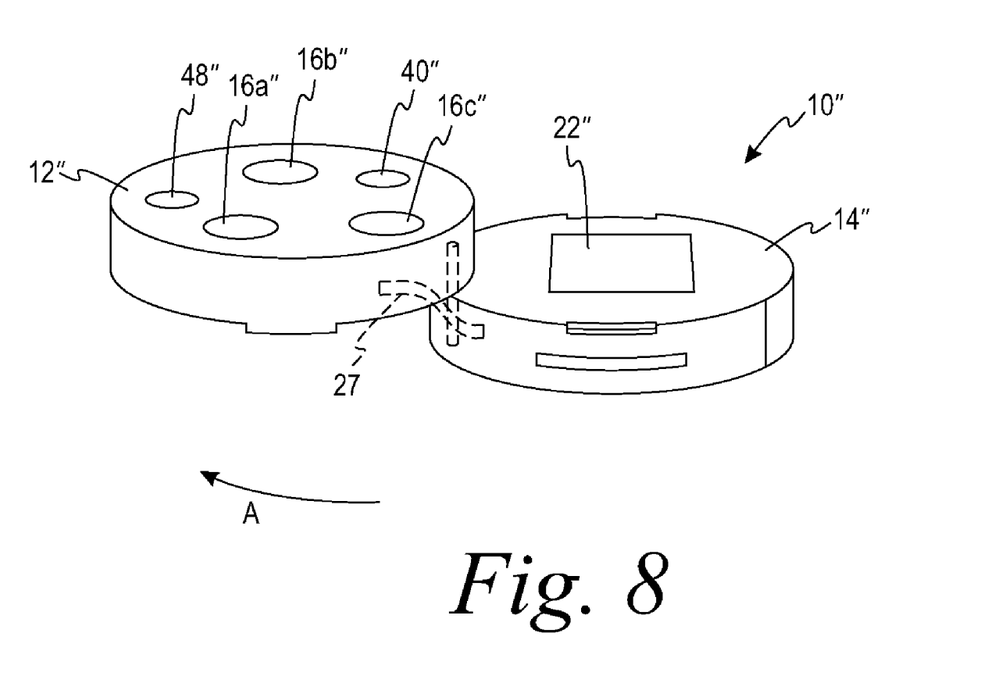
FIG. 8 is a top perspective view of a meter in an open position according to another embodiment of the present invention.

The second portion 14 may be connected electrically to the first portion 12 by a flexible circuit cable 27 (see FIG. 8). It is contemplated that other mechanisms suitable for electrically connecting the first portion 12 to the second portion 14 may also be used.

In the embodiment of FIGS. 1a,b, the display 22 is positioned on an outwardly-facing surface of the first portion 12, and the user-interface buttons 16a-c are positioned on an inwardly-facing surface of second portion 14. This embodiment may be desirable so that a user may input information into the meter 10 via the user-interface buttons 16a-c and instantaneously view the information on the display 22. When the meter 10 is in the closed position of FIG. 1b, the user-interface buttons 16a-c are generally hidden. Thus, the user-interface buttons 16a-c are generally protected from, for example, accidental depression. Because the display 22 is exposed in both the open and closed positions, the meter 10 may have an optional feature for protecting the display 22 from scratches or other damage, including, but not limited to, a removable cover 29 (see FIG. 1A).

In another embodiment, a meter includes a user-interface mechanism positioned on an outwardly-facing surface of a first portion and a display positioned on an inwardly-facing surface of a second portion (see FIG. 8). When the meter of this embodiment is in a closed position, the display is generally hidden. Thus, the display is generally protected from, for example, scratches or other damage. Because the user-interface mechanism is exposed in both open and closed positions, the meter may have an optional feature for protecting the user-interface mechanism from, for example, accidental depression. For example, the meter may include an electronic lock-out feature, whereby the meter may not be activated (i.e., via the user-interface mechanism) unless the meter is in an open position. It is contemplated that other features suitable for protecting the user-interface mechanism from accidental activation may also be implemented.

Figure 7:
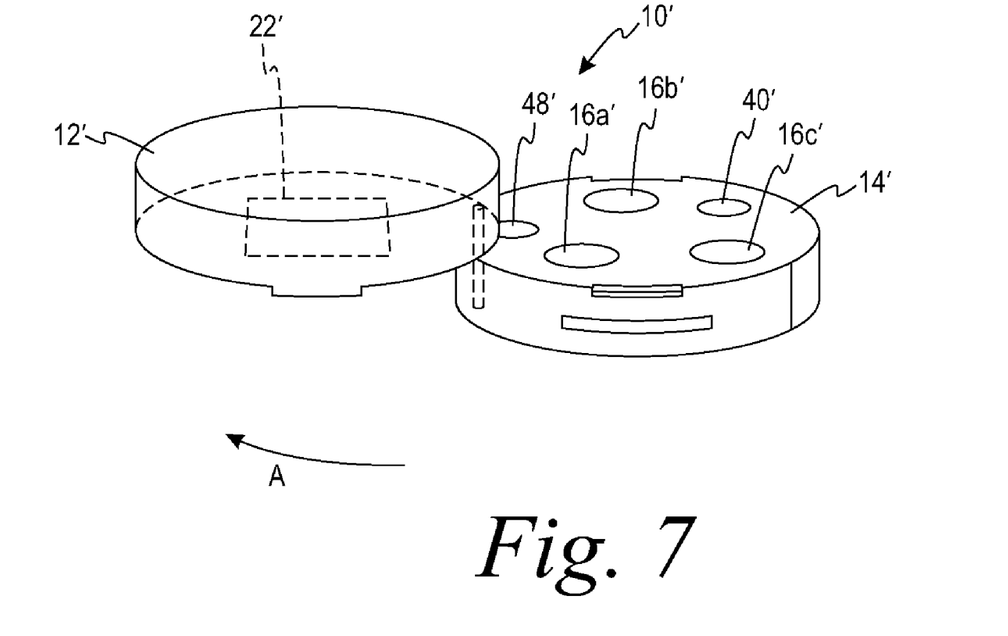
FIG. 7 is a top perspective view of a meter in an open position according to another embodiment of the present invention.

In yet another embodiment, a meter includes a display and a user-interface mechanism positioned on internally-facing surfaces of respective first and second portions (see FIG. 7). When the meter of this embodiment is in a closed position, the display and the user-interface mechanism are adjacent to each other and hidden from view. Thus, in the closed position, the display is generally protected from damage and scratching, and the risk of accidentally depressing the user-interface mechanism is minimized or eliminated.

Figure 2A:
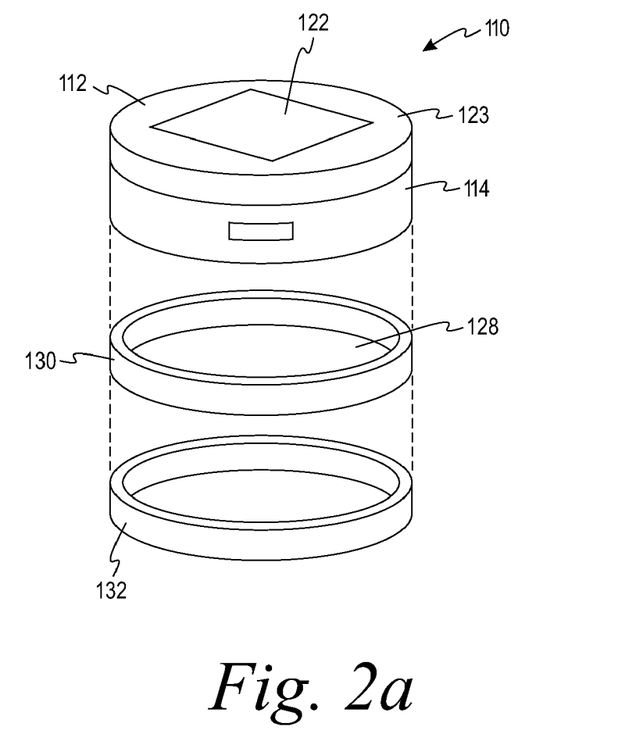
FIG. 2a is a top perspective view of a meter having a plurality of compartments, according to another embodiment of the present invention.
Figure 2B:
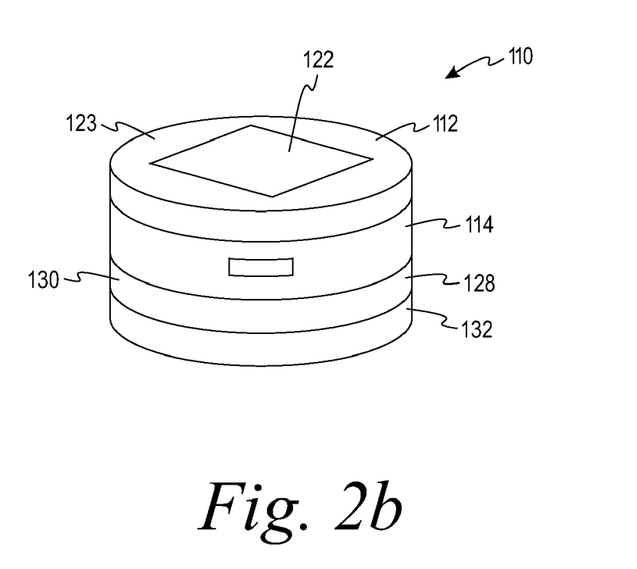

The meter of the present invention may include at least one compartment for storing analyte-testing instruments to enhance the storage capabilities and convenience to a user, as shown in FIGS. 2a,b. The meter 110 has generally the same structure as the meter 10 of FIGS. 1a,b. The meter 110 further includes at least one compartment 128 for storing, for example, glucose-testing instruments. The glucose-testing instruments may include, but are not limited to, lancets, test sensors, and/or tissues. The at least one compartment 128 may be, for example, a snap-on compartment, a screw-on compartment, a flip-top compartment hingedly coupled to the meter 110, or the like. Other mechanisms suitable for coupling the at least one compartment 128 to the meter 110 may also be used. Each compartment 128 may be further divided into sub-compartments (not shown) so that a user may store several types of analyte-testing instruments within a single compartment 128 without intermingling the analyte-testing instruments. Although in the illustrated embodiment, the at least one compartment 128 is shown coupled to a second portion 114, it is contemplated that the at least one compartment 128 may alternatively or additionally be coupled to another portion of the meter 110 (i.e., the first portion 112). Alternatively, or in addition to, the at least one additional compartment 128, one or more of the first portion 112 and the second portion 114 may include compartments, drawers, or the like for storing analyte-testing instruments.

The meter 110 of FIGS. 2a,b includes a plurality of generally vertically stacked compartments 128, which includes a first compartment 130 and a second compartment 132. FIG. 2b is an exploded view of the meter 110 of FIG. 2a. In embodiments where the meter 110 includes a plurality of compartments 128, the meter 110 may generally contain substantially all or all of the items used for analyte-testing within the plurality of compartments 128 such that the meter 110 may be a "one-stop" analyte-testing instrument for a user. For example, the first compartment 130 may contain unused lancets. The second compartment 132 may contain individually unused test sensors or an unused cartridge that contains a plurality of unused test sensors. It is contemplated that the meter 110 may include other compartments, for example, to store individually used test sensors or a used cartridge that contains a plurality of used test sensors, a plurality of tissues for cleaning, or other items.

Figure 3A:
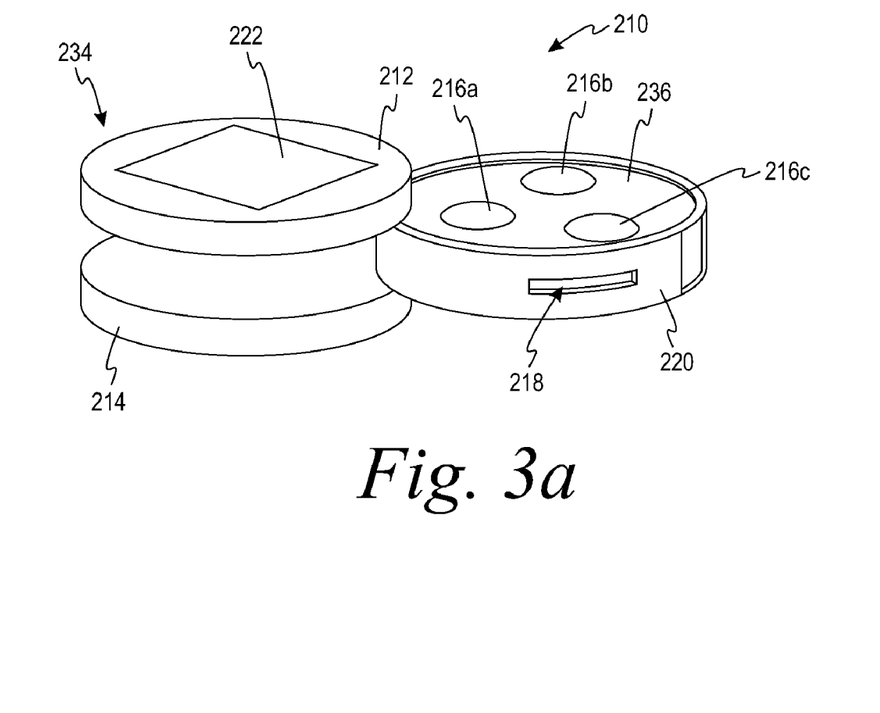
FIG. 3a is a front perspective view of a meter in an open position according to another embodiment of the present invention.
Figure 3B:
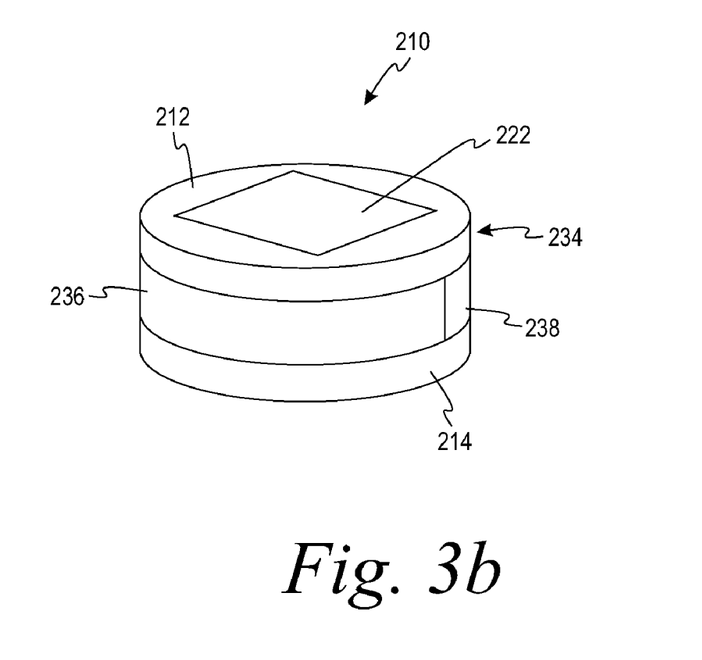
FIG. 3b is a front perspective view of the meter of FIG. 3a in a closed position.

Referring now to the embodiment of FIGS. 3a,b, a meter 210 comprises a main housing 234, which includes a first portion 212 and a second portion 214, and a middle portion 236. The meter 210 may also include a wall portion 238 that generally extends along a portion of the circumference (e.g., half of the circumference) of the meter 210 and couples the first portion 212 and the second portion 214. The wall portion 238 generally has a thickness ranging from approximately 0.15 in. to approximately 0.30 in. The height of the wall portion 238 is slightly larger than the height of the middle portion 236. The meter 210 includes a display 222 positioned on the first portion 212. The middle portion 236 includes a user-interface mechanism (e.g., buttons 216a-c) and forms at least one test-sensor opening 218 therein positioned on a side surface 220. The second portion 214 generally includes a battery.

When the meter 210 is in a closed position of FIG. 3b, a portion of the wall section 238 is adjacent to and substantially flush with a portion of the side surface 220 of the middle portion 236. The portion of the side surface adjacent to the wall portion 236 may include the test-sensor opening 218 such that, when the meter 210 is in the closed position, the test-sensor opening 218 may be hidden behind the wall portion 238. This may be desirable so that the amount of dust or other contaminants entering the meter 210 through the test-sensor opening 218 may be minimized. Moreover, when the meter 210 is in the closed position, the user-interface buttons 216a-c are concealed beneath the first portion 212. Thus, the risk of the meter 210 being accidentally activated by depressing the user-interface buttons 216a-c is minimized or eliminated.

It is further contemplated that the meter 210 may have additional compartments coupled to the first portion 212 and/or the second portion 214, such as the compartments 130, 132 shown in FIGS. 2a,b and described above. Moreover, the meter 210 may have a removable cover (not shown) coupled to the first portion to protect the display 222 from scratches or other damage while being, for example, transported or carried. The cover may snap-on, screw-on, or be hingedly coupled to the first portion 212.

Figure 4A:
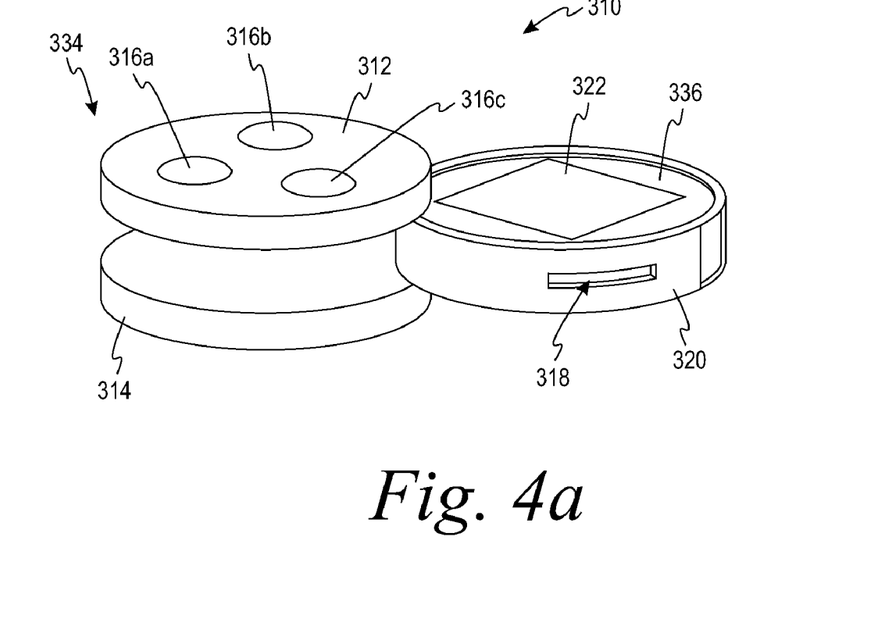
FIG. 4a is a front perspective view of a meter in an open position according to another embodiment of the present invention.
Figure 4B:
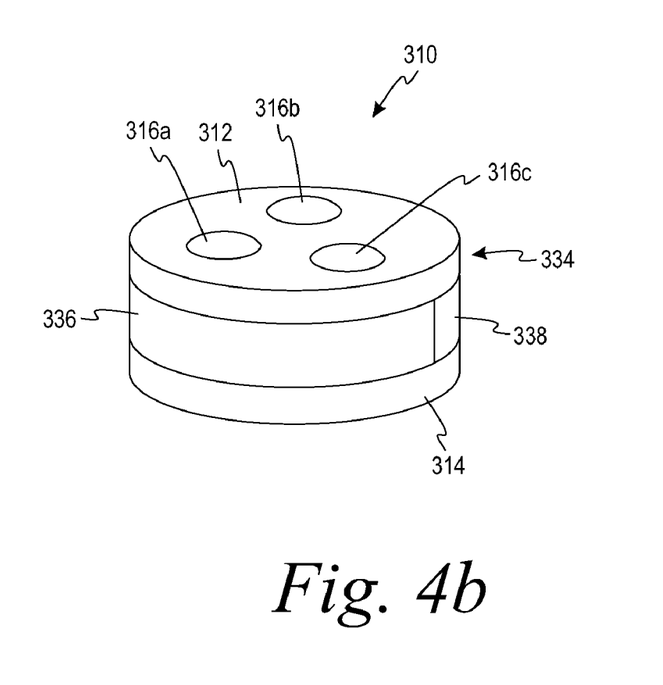
FIG. 4b is a front perspective view of the meter of FIG. 4a in a closed position.

In an alternative embodiment illustrated in FIGS. 4a,b, a meter 310 has generally the same structure as the meter 210 of FIGS. 3a,b. However, in the embodiment of FIGS. 4a,b, the meter 310 includes a user-interface (e.g., buttons 316a-c) positioned on a first portion 312 and a display 322 located on a middle portion 336. When the meter 310 is in a closed position, as shown in FIG. 4b, the display 322 is hidden from view. Thus, the display 322 is generally protected from damage and scratching when the meter 310 is in the closed position while being, for example, transported or carried. Because the user-interface buttons 316a-c are located on the first portion 312, they are exposed both when the meter 310 is in an open position (FIG. 4a) and in the closed position (FIG. 4b). Thus, the meter 310 of this embodiment may optionally include a feature to minimize the risk of the user-interface buttons 316a-c being accidentally activated. For example, the meter 310 may include an electronic lock-out feature, whereby the meter 310 may not be activated (i.e., via the user-interface buttons 316a-c) unless the meter 310 is in the open position. It is contemplated that other features suitable for protecting the user-interface buttons 316a-c from accidental activation may also be implemented.

It is contemplated that the number of user-interface buttons on the instrument may be different than depicted in the illustrated embodiments. Additional functionalities may be provided to offer the user a means to input notes into the memory. For example, the number of buttons may be increased so that the user may input a note into the memory to record that he or she had exercised, eaten, taken a medication prior to testing, or the like. Thus, the user may store an electronic log along with a glucose reading history within the instrument. The buttons may also be used to set and display date and time information and to activate alarms that remind the user to conduct, for example, a blood glucose test according to a predetermined schedule. The buttons may also be used to activate certain calibration procedures for the meter. It may be desirable for the buttons to be larger to assist those individuals with poor hand/finger coordination and/or poor vision. For example, the buttons may have a diameter of at least 0.25 inch. It is contemplated that the buttons may be shaped differently than those shown in the illustrated embodiments.

According to another embodiment, the display may communicate in an audible manner instead of or in addition to the above-discussed visual manner. Thus, the display may be designed to operate in audible and visual manners.

If electrochemical test sensors are used in the meter of the present invention, then one of the test sensors will be properly aligned with one or more electrical contacts housed within the meter. The testing end of the sensor then receives, for example, a drop of blood to be tested, whereby the blood is analyzed by the electrochemical circuit. The results of the analysis are then displayed on the display of the meter. It is contemplated that other types of sensors may be used, such as optical sensors.

A test sensor may be removed from, for example, one of the compartments 128 (see FIGS. 2a,b) and manually placed in the test-sensor opening 18 (see, e.g., FIG. 1a-b). According to another process, a test sensor may be automatically advanced to the test-sensor opening 18 by utilizing the user-interface (e.g., the user pressing one of the buttons 16a-c). Alternatively, the test sensor may be advanced mechanically during, for example, the act of opening the case. The meter is generally turned on after the test sensor is placed into or advanced into the test-sensor opening 18. After the meter 10 is powered on, the testing is ready to begin.

The user typically places his/her finger up to a lancet or a lancing device to generate a whole blood sample. It is contemplated that a blood sample may be generated from other areas of the body. The user then removes his/her finger from the lancet or lancing device and brings the whole blood sample into contact with the sensor, in which the blood is generally drawn into the sensor by capillary action. The test sensors are typically provided with a capillary channel that extends from the front or testing end of the sensors to biosensing or reagent material disposed in the sensor. The biosensing or reagent material is designed to react with the desired analyte to be tested. When the testing end of the sensor is placed into fluid (e.g., blood that is accumulated on a person's finger after the finger has been pricked), a portion of the fluid is drawn into the capillary channel by capillary action. The fluid then chemically reacts with the reagent material in the sensor so that an electrical signal indicative of the blood glucose level being tested is supplied and subsequently transmitted to an electrical assembly.

After a minimum amount of blood is drawn into the test sensor, the testing is performed and the result is, for example, shown on the display and stored in memory. The result of the testing may also be announced audibly, by, for example, using a speaker, and stored in memory.

After the testing has been completed, the test sensor may be removed from the test-sensor opening 18 by several methods. In one embodiment, the meter 10 may include an eject mechanism 40 that ejects the used test sensor from the meter 10 (see FIG. 1a). In such an embodiment, the test sensors are released forcefully. In a further embodiment, the test sensor may be removed manually from the meter 10.

Figure 5A:
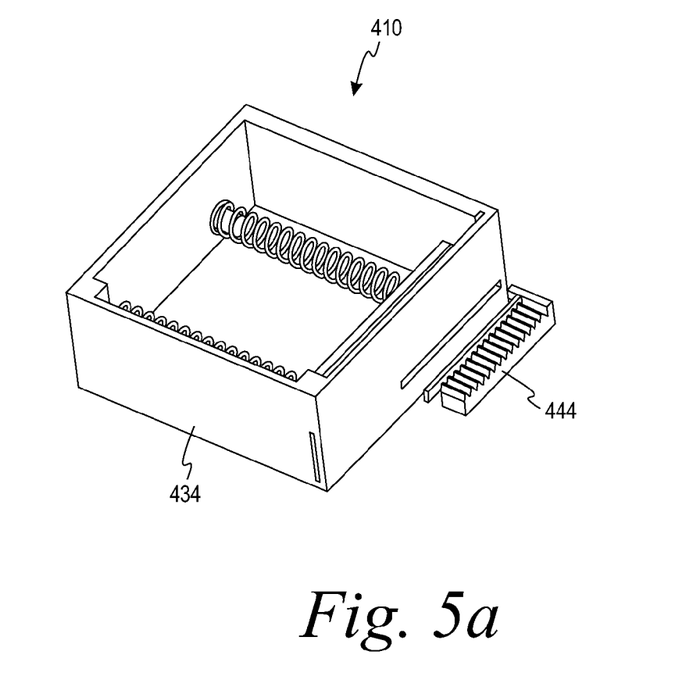
FIG. 5a is a perspective internal view of a test-sensor cartridge according to one embodiment.
Figure 5B:
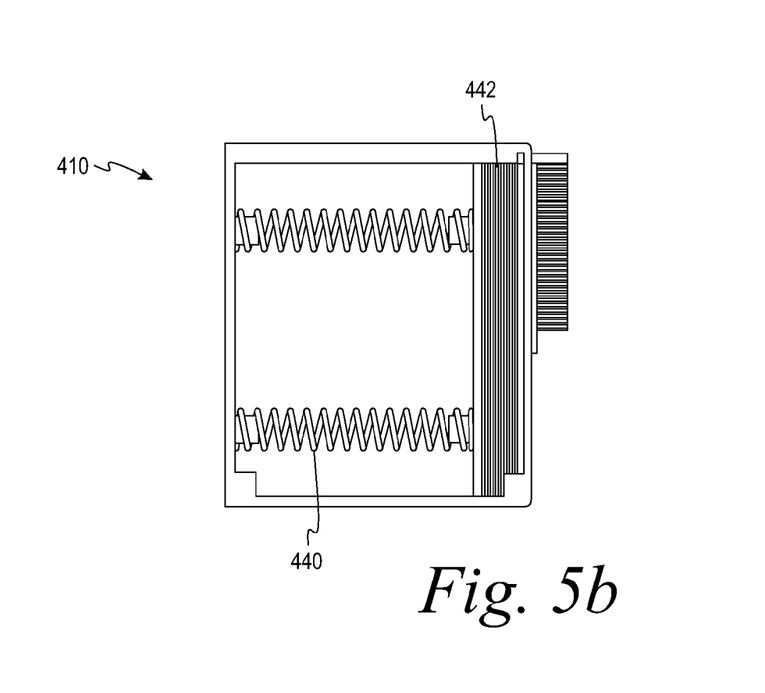
Figure 6:
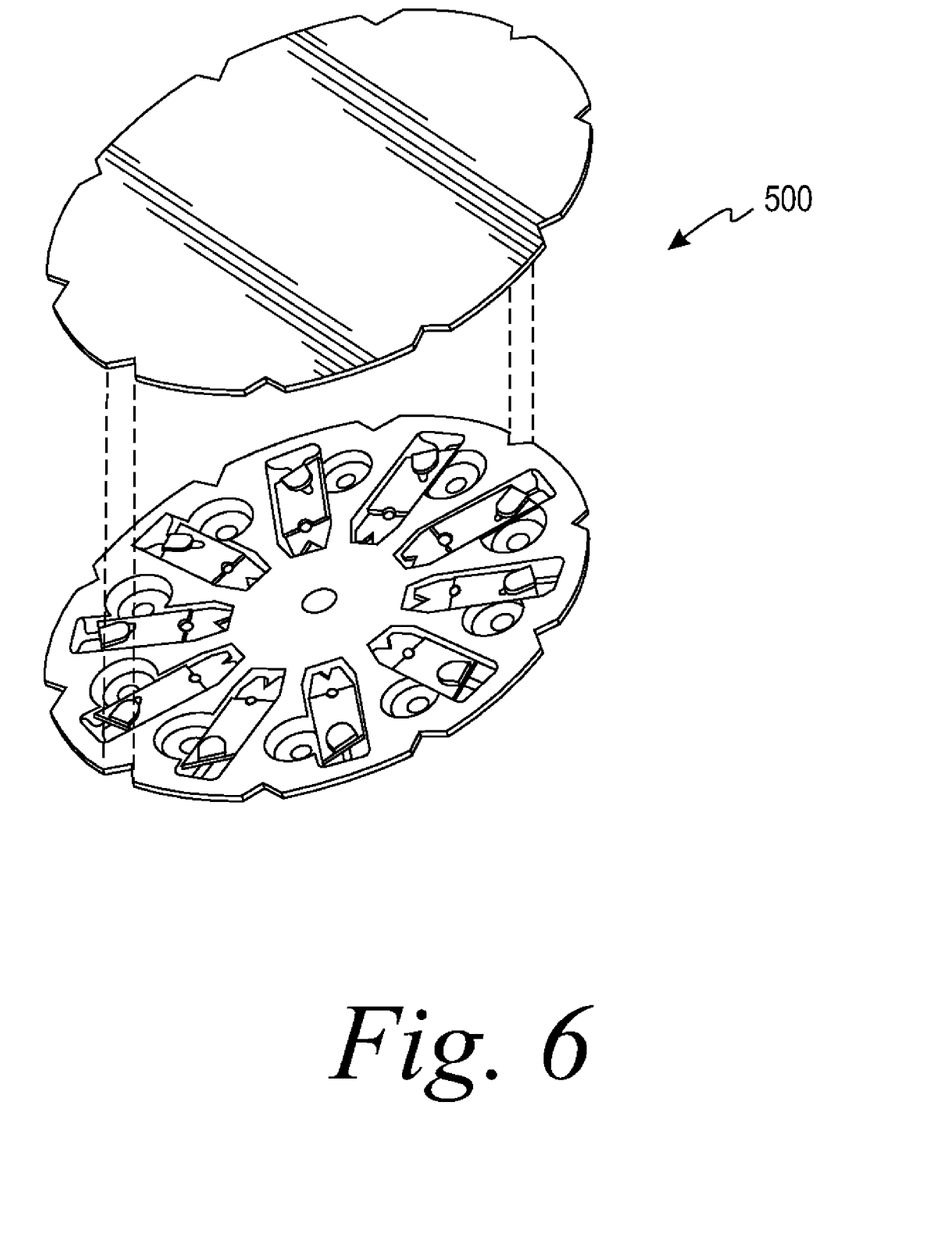
FIG. 6 is a top perspective view of a test sensor cartridge according to another embodiment.

According to another embodiment, a disposable cartridge that contains a plurality of test sensors may be used. One example of a disposable cartridge 410 that may be used in the meter 10 is depicted in FIGS. 5a,b. The disposable cartridge 410 of FIGS. 5a,b comprises a housing 434, a plurality of stacked test sensors 442, a movable mechanism 444, a mechanical mechanism 446, and a plurality of moveable seals (not shown). The cartridge 410 is adapted to be disposable after each of the plurality of test sensors 442 has been used. After each of the plurality of test sensors 442 has been used, the cartridge 410 may be removed from the meter or a compartment 128 (see FIGS. 2a,b) within the meter and replaced with a second identical cartridge that includes a plurality of unused test sensors. Another type of cartridge that may be used with the present invention is a blister-type pack 500, where the sensors are individually packaged in sensor cavities, as shown in FIG. 6.

The meters of the present invention (e.g., meter 10) according to a further embodiment may include a programmable alarm 48 to alert the user to begin testing (see FIG. 1a). The alarm 48 is programmed to sound at a predetermined schedule. An alarm is especially useful for those individuals who have poor memory as well as those individuals who become easily preoccupied and/or forget to test according to a predetermined schedule.

The meters of the present invention (e.g., meter 10) may include a built-in data management system 50 that is accessible to remote monitoring by, for example, a physician. Such a built-in data management system 50 may be connected for remote monitoring by, for example, a telephone line 52 and a modem 54 (see FIG. 1b). In addition or alternatively, the meter 10 may be connected to a computerized data management system so that, for example, a user may download and save results and information regarding previous glucose tests.

The meters of the present invention (e.g., meter 10) may also include a bar code reader that reads a bar code label on a disposable test-sensor cartridge. The bar code reader may determine information such as the lot number and calibration numbers for a particular test sensor being used.

It is also contemplated that the meters of the present invention (e.g., meter 10) may be sealed so as to make it water-resistant. The compact size of the meter 10 combined with a water-resistant feature may appeal particularly to young, active, and/or athletic users.

Alternative Embodiment A

A foldable instrument adapted to determine an analyte concentration of a fluid sample using a test sensor, the instrument comprising:

a first portion including a display; and a second portion pivotally coupled to the first portion by a pivot mechanism, the second portion including a user-interface mechanism, wherein one of the first portion and second portion includes at least one opening formed therein, the opening being adapted to receive a test sensor, wherein the instrument is adapted to be folded into a closed position and unfolded into an open position by rotating one of the first portion and second portion about the pivot mechanism.

Alternative Embodiment B

The instrument of Alternative Embodiment A wherein the instrument has a generally circular cross section.

Alternative Embodiment C

The instrument of Alternative Embodiment A, wherein the first portion and the second portion have substantially the same shape.

Alternative Embodiment D

The instrument of Alternative Embodiment A, wherein one of the first portion and the second portion includes a battery.

Alternative Embodiment E

The instrument of Alternative Embodiment A, wherein the user-interface mechanism is at least one button.

Alternative Embodiment F

The instrument of Alternative Embodiment A, wherein the display and the user-interface are positioned on internally-facing surfaces of the respective first and second portions.

Alternative Embodiment G

The instrument of Alternative Embodiment A, wherein the display is positioned on an internally-facing surface of the first portion, and wherein the user-interface mechanism is positioned on an externally-facing surface of the second portion.

Alternative Embodiment H

The instrument of Alternative Embodiment A, wherein the display is positioned on an externally-facing surface of the first portion, and wherein the user-interface mechanism is positioned on an internally-facing surface of the second portion.

Alternative Embodiment I

The instrument of Alternative Embodiment H, further comprising a removable cover adapted to cover the display.

Alternative Embodiment J

The instrument of Alternative Embodiment A, further comprising at least one compartment coupled to one of the first portion and the second portion, the at least one compartment being adapted to store at least one analyte-testing instrument.

Alternative Embodiment K

The instrument of Alternative Embodiment J, wherein the at least one compartment is a plurality of stacked compartments.

Alternative Embodiment L

The instrument of Alternative Embodiment A, wherein the instrument has a footprint of less than 5 in$^2$.

Alternative Embodiment M

The instrument of Alternative Embodiment L, wherein the display has an area of at least 1 in$^2$.

Alternative Embodiment N

The instrument of Alternative Embodiment A, wherein the instrument is water-resistant.

Alternative Embodiment O

The instrument of Alternative Embodiment A, wherein the first portion and the second portion are adapted to releasably lock therewith.

Alternative Embodiment P

The instrument of Alternative Embodiment A, wherein the first portion and the second portion are electrically connected by a flexible circuit cable.

Alternative Embodiment Q

A foldable instrument adapted to determine an analyte concentration of a fluid sample using a test sensor, the instrument comprising:
a main housing including a first portion and a generally parallel second portion, the second portion being coupled to the first portion by a wall portion;
a middle portion positioned between the first portion and the second portion, the middle portion including at least one opening formed therein, the opening being adapted to receive a test sensor, the middle portion being pivotally coupled to at least one of the first portion and the second portion by a pivot mechanism;
a display positioned on one of the first portion and the middle portion; and
a user-interface mechanism positioned on one of the first portion and the middle portion not including the display,
wherein the instrument is adapted to be folded into a closed position and unfolded into an open position by rotating at least one of the main housing and the middle portion about the pivot mechanism.

Alternative Embodiment R

The instrument of Alternative Embodiment Q, wherein the instrument has a generally circular cross section.

Alternative Embodiment S

The instrument of Alternative Embodiment Q, wherein the first portion, the second portion, and the middle portion have substantially the same shape.

Alternative Embodiment T

The instrument of Alternative Embodiment Q, wherein the first portion includes the display and wherein the middle portion includes the user-interface mechanism.

Alternative Embodiment U

The instrument of Alternative Embodiment T, further comprising a removable cover adapted to cover the display.

Alternative Embodiment V

The instrument of Alternative Embodiment Q, wherein the first portion includes the user-interface mechanism and wherein the middle portion includes the display.

Alternative Embodiment W

The instrument of Alternative Embodiment Q, wherein the second portion includes a battery.

Alternative Embodiment X

The instrument of Alternative Embodiment Q, wherein the user-interface mechanism is at least one button.

Alternative Embodiment Y

The instrument of Alternative Embodiment Q, wherein the test-sensor opening is adjacent to the wall portion when the instrument is in the closed position.

Alternative Embodiment Z

The instrument of Alternative Embodiment Q, further comprising at least one compartment coupled to at least one of the first portion and the second portion, the at least one compartment being adapted to store analyte-testing instruments.

Alternative Embodiment AA

The instrument of Alternative Embodiment Z, wherein the at least one compartment is a plurality of stacked compartments.

Alternative Embodiment AB

The instrument of Alternative Embodiment Q, wherein the instrument has a footprint of less than 5 in$^2$.

Alternative Embodiment AC

The instrument of Alternative Embodiment Q, wherein the display has an area of at least 1 in$^2$.

Alternative Embodiment AD

The instrument of Alternative Embodiment Q, wherein the instrument is water-resistant.

Alternative Embodiment AE

The instrument of Alternative Embodiment Q, wherein the middle portion and the main housing are adapted to releasably lock therewith.

Alternative Embodiment AF

The instrument of Alternative Embodiment Q, wherein the first portion, the second portion, and the middle portion are electrically connected by a flexible circuit cable.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents, combinations, and alternatives falling within the spirit and scope of the invention as defined by the appended claims.

The invention claimed is:

1. A foldable instrument adapted to determine an analyte concentration of a fluid sample using a test sensor, the instrument comprising:
   a first portion including a display and a first internally-facing surface; and
   a second portion pivotally coupled to the first portion by a pivot mechanism, the second portion including a user-interface mechanism and a second internally-facing surface,
   wherein one of the first portion and second portion includes at least one opening formed therein, the opening being adapted to receive a test sensor,
   wherein the instrument is adapted to be folded into a closed position and unfolded into an open position by rotating one of the first portion and second portion about the pivot mechanism in a direction generally parallel to the entire first and second internally-facing surfaces.

2. The instrument of claim 1, wherein the instrument has a generally circular cross section.

3. The instrument of claim 1, wherein the first portion and the second portion have substantially the same shape.

4. The instrument of claim 1, wherein the user-interface mechanism includes at least one button.

5. The instrument of claim 1, wherein the display and the user-interface are positioned on the first and second internally-facing surfaces of the respective first and second portions.

6. The instrument of claim 1, wherein the display is positioned on the first internally-facing surface of the first portion, and wherein the user-interface mechanism is positioned on an externally-facing surface of the second portion.

7. The instrument of claim 1, wherein the display is positioned on an externally-facing surface of the first portion, and wherein the user-interface mechanism is positioned on the second internally-facing surface of the second portion.

8. The instrument of claim 7, further comprising a removable cover adapted to cover the display.

9. The instrument of claim 1, further comprising at least one compartment coupled to one of the first portion and the second portion, the at least one compartment being adapted to store at least one analyte-testing instrument.

10. The instrument of claim 1, wherein the instrument has a footprint of less than 5 in$^2$.

11. The instrument of claim 10, wherein the display has an area of at least 1 in$^2$.

12. The instrument of claim 1, wherein the first portion and the second portion are adapted to releasably lock therewith.

13. The instrument of claim 1, wherein the first portion and the second portion are electrically connected by a flexible circuit cable.

14. A foldable instrument adapted to determine an analyte concentration of a fluid sample using a test sensor, the instrument comprising:
   a main housing including a first portion and a generally parallel second portion, the second portion being coupled to the first portion by a wall portion;
   a middle portion positioned between the first portion and the second portion, the middle portion including at least one opening formed therein, the opening being adapted to receive a test sensor, the middle portion being pivotally coupled to at least one of the first portion and the second portion by a pivot mechanism;
   a display positioned on one of the first portion and the middle portion; and
   a user-interface mechanism positioned on one of the first portion and the middle portion not including the display,
   wherein the instrument is adapted to be folded into a closed position and unfolded into an open position by rotating at least one of the main housing and the middle portion about the pivot mechanism along a plane generally parallel to both the main housing and the middle portion.

15. The instrument of claim 14, wherein the instrument has a generally circular cross section.

16. The instrument of claim 14, wherein the first portion, the second portion, and the middle portion have substantially the same shape.

17. The instrument of claim 14, wherein the first portion includes the display and wherein the middle portion includes the user-interface mechanism.

18. The instrument of claim 14, wherein the first portion includes the user-interface mechanism and wherein the middle portion includes the display.

19. The instrument of claim 14, wherein the test-sensor opening is adjacent to the wall portion when the instrument is in the closed position.

20. The instrument of claim 14, further comprising at least one compartment coupled to at least one of the first portion and the second portion, the at least one compartment being adapted to store analyte-testing instruments.

21. The instrument of claim 14, wherein the first portion includes a first internally-facing surface and the second portion includes a second internally-facing surface, the at least one of the main housing and the middle portion being rotated in a direction generally parallel to the first and second internally-facing surfaces.

22. A foldable instrument adapted to determine an analyte concentration of a fluid sample using a test sensor, the instrument comprising:
- a main housing including a first portion and a generally parallel second portion, the second portion being coupled to the first portion by a wall portion, the main housing having a first internally facing surface;
- a middle portion positioned between the first portion and the second portion, the middle portion including at least one opening formed therein, the opening being adapted to receive a test sensor, the middle portion being pivotally coupled to at least one of the first portion and the second portion by a pivot mechanism, the middle portion having a second internally facing surface;
- a display positioned on one of the first portion and the middle portion; and
- a user-interface mechanism positioned on one of the first portion and the middle portion not including the display,
- wherein the instrument is adapted to be folded into a closed position and unfolded into an open position by rotating at least one of the main housing and the middle portion about the pivot mechanism in a direction generally parallel to the entire first and second internally-facing surfaces.

* * * * *